United States Patent [19]
DeRock

[11] Patent Number: 5,465,045
[45] Date of Patent: Nov. 7, 1995

[54] EDDY CURRENT PROBE WITH DEFLECTABLE SIDEWALLS

[76] Inventor: Richard DeRock, 757 First Ave., Gibbon, Minn. 55335

[21] Appl. No.: 143,879

[22] Filed: Oct. 28, 1993

[51] Int. Cl.⁶ .......................... G01N 27/90; G01N 27/87; G01R 33/12
[52] U.S. Cl. .............................. 324/220; 324/262
[58] Field of Search ..................... 324/219, 220, 324/221, 226, 233, 234, 236, 239, 340, 243, 262

[56] References Cited

U.S. PATENT DOCUMENTS

| | | | |
|---|---|---|---|
| 4,063,157 | 12/1977 | Lorenzi et al. | 324/220 X |
| 4,139,822 | 2/1979 | Urich et al. | 324/219 |
| 4,153,875 | 5/1979 | Pigeon et al. | 324/220 |
| 4,262,425 | 4/1981 | Sabato | 33/178 R |
| 4,303,884 | 12/1981 | Malick | 324/220 |
| 4,625,165 | 11/1986 | Rothstein | 324/220 |
| 4,797,613 | 1/1989 | Wentzell | 324/220 |
| 4,937,524 | 6/1990 | Fasnacht et al. | 324/220 |
| 4,992,735 | 2/1991 | Cullen et al. | 324/220 |
| 5,023,549 | 6/1991 | Dau et al. | 324/220 |
| 5,059,904 | 10/1991 | Mazzone et al. | 324/219 X |
| 5,136,240 | 8/1992 | Geier et al. | 324/220 |
| 5,247,251 | 9/1993 | Yost et al. | 324/220 |
| 5,254,944 | 10/1993 | Holmes et al. | 324/220 |

FOREIGN PATENT DOCUMENTS

| | | | |
|---|---|---|---|
| 55-60805 | 5/1980 | Japan | 324/220 |
| 1173294 | 8/1985 | U.S.S.R. | 324/220 |

*Primary Examiner*—Sandra L. O'Shea
*Assistant Examiner*—Warren S. Edmonds
*Attorney, Agent, or Firm*—Merchant, Gould, Smith, Edell, Welter & Schmidt

[57] ABSTRACT

An eddy current probe of a type used in testing for defects in material surrounding a bolt hole. The probe includes an eddy current coil mounted on one of a plurality of flexible sidewalls that insert into a bolt hole. The probe further includes a knob that rotates to move the flexible sidewalls radially relative to the longitudinal axis of the bolt hole.

20 Claims, 3 Drawing Sheets

EDDY CURRENT PROBE WITH DEFLECTABLE SIDEWALLS

FIELD OF THE INVENTION

The present invention relates to eddy current probes that can be used to detect defects in material surrounding bolt holes and the like.

BACKGROUND OF THE INVENTION

Eddy current testing is a well known process in which a small coil of wire is used to produce an electromagnetic field proximate a conductive material. The electromagnetic field interacts with the conductive material to induce an eddy current, which in turn produces a secondary electromagnetic field of opposite polarity to the primary field. The coil is connected to instruments that monitor the effect of the interacting fields on the coil, in addition to providing the current that produces the primary electromagnetic field. In the absence of defects in the conductive material, the eddy current signals are relatively small in amplitude, and the monitor interprets the electrical characteristics of the coil accordingly. On the other hand, a defect or discontinuity in the conductive material interrupts the paths of the eddy currents, causing a measurable increase in the amplitude of the eddy current signals, and the monitor interprets the change in the electrical characteristics of the coil accordingly. The increase in signal amplitude is a function of the size of the discontinuity in the conductive material.

Eddy current testing has a wide range of applications, including detection of defects in aircraft parts and other types of high speed turbomachinery having bolt holes formed therein. In this particular application, one of several probes is selected according to the diameter of the bolt hole, and the chosen probe is connected to conventional eddy current testing equipment. The system is calibrated for the chosen probe, and then the probe is inserted into the bolt hole so that an eddy current coil on the probe is proximate the side of the bolt hole.

One type of eddy current probe, commonly known as a non-contacting probe, has a fixed diameter approximately 10 mils less than the diameter of the bolt hole to be inspected. The probe is rotated at approximately 1500 rpm as it is inserted into the bolt hole. Since the quality of the inspection is a function of the proximity of the eddy current coil to the wall of the bolt hole, a separate probe is required for each variation in bolt hole diameter that exceeds 5 mils.

Another type of eddy current probe, commonly known as a contact probe, has a diameter no smaller than 20 mils less than the diameter of the bolt hole to be inspected, and no greater than 5 mils more than the diameter of the bolt hole to be inspected. This type of probe also requires calibration of the operating system each time a different probe is connected thereto. The contact probe is rotated at approximately 500 rpm as it is inserted into the bolt hole. In order to position the coil as close as possible to the wall of the bolt hole, this type of probe is biased into contact with the bolt hole wall. To accomplish this biasing, the conventional contact probe has an eddy current coil mounted on one of a pair of flexible fingers. If the effective diameter of the relaxed fingers is slightly greater than the diameter of the bolt hole, then the probe is simply wedged into the bolt hole. If the effective diameter of the relaxed fingers is less than the diameter of the bolt hole, then a wedge is inserted between the distal ends of the fingers to force them outward into contact with the wall of the bolt hole. Although somewhat tedious, this wedging technique is suitable for varying the effective diameter by as much as 25 mils.

Both of the probes described above suffer from their relative lack of diameter adjustability, because bolt hole diameters vary significantly. Changing probes and recalibrating the system for each newly substituted probe is time consuming. Moreover, a complete bolt hole inspection set must include a series of eddy current probes ranging in effective size from the diameter of the smallest encountered bolt hole to the diameter of the largest encountered bolt hole. Even with the adjustability afforded by wedging the conventional contact probe, seventeen such probes are required to inspect bolt holes ranging in diameter from 0.200 inches to 0.600 inches. The need to stock so many functionally identical tools is expensive, as well as inconvenient. Accordingly, a need exists for an eddy current probe that is capable of inspecting bolt holes ranging significantly more than 25 mils in diameter.

Others have recognized this need for an adjustable diameter bolt hole probe, as evidenced by U.S. Pat. Nos. 4,262,425 and 5,136,240, both of which disclose self-adjusting eddy current probes. Although on paper, each of these patented devices may appear to solve the need for adjustability, in practice, neither of these devices has been particularly well received in the industry. The devices provide a greater range of adjustability but not without shortcomings. For example, both patented devices, as well as the "wedgeable" contact probe described above, have sidewalls that flex in an arc toward the wall of the bolt hole to be tested, thereby varying the angle of the eddy current coil relative to the bolt hole wall.

Another problem arises from the fact that each of the self-adjusting devices has an outwardly biased expansion mechanism that provides an expansion bias as a function of the magnitude of expansion. In other words, the eddy current coil is pressured more against the wall of a bolt hole having a relatively small diameter, and less against the wall of a bolt hole having a relatively larger diameter. Accordingly, calibration may still be required between tests of different sized bolt holes, even though the same probe may be used in both tests. Moreover, it is unclear to what extent either of these patented devices eliminates the need for multiple probes. In this regard, it is believed that the device disclosed in U.S. Pat. No. 5,136,240 might expand from a minimum diameter of 0.250 inches to a maximum diameter of 0.300 inches, for example.

Another problem with the outwardly biased expansion mechanisms is that the probe could become stuck if it were accidentally inserted all the way through a bolt hole, because the sidewalls would be biased beyond the confines of the bolt hole. In view of the foregoing, the need remains for an effective bolt hole probe having an adjustable diameter range of several tenths of an inch.

SUMMARY OF THE INVENTION

In one respect, the present invention provides an eddy current probe that includes a tube and a shaft movably mounted within the tube. The tube has a longitudinal axis and flexible sidewalls that extend substantially parallel to the longitudinal axis. Movement of the shaft relative to the tube causes radial deflection of the flexible sidewalls relative to the longitudinal axis. An eddy current coil is mounted on one of the flexible sidewalls and maintains a fixed orientation during deflection of the sidewalls.

In another respect, the present invention provides an eddy current probe that includes a first member, a second member having a first end secured to the first member, and a third member having a first end movably connected to the first member, and a second, opposite end secured to a second, opposite end of the second member. The second member has flexible sidewalls disposed between its first and second ends, and movement of the third member relative to the first member causes the flexible sidewalls to deflect outward. An eddy current sensing means is mounted on one of the flexible sidewalls.

In yet another respect, the present invention provides an eddy current testing system of a type used to detect defects in material surrounding bolt holes. The system includes a probe having flexible sidewalls that are movable from first positions defining a first, relatively smaller effective diameter to second positions defining a second, relatively larger effective diameter. An adjusting means is rotatably mounted relative to the probe for moving the flexible sidewalls from the first positions to the second positions. Rotation of the adjusting means in one direction moves the flexible sidewalls toward the second, relatively larger effective diameter, and rotation of the adjusting means in an opposite direction moves the flexible sidewalls toward the first, relatively smaller effective diameter. An eddy current coil is secured to at least one of the flexible sidewalls, and an operating means is connected to the probe for energizing the coil within the bolt hole and analyzing whether and to what extent a defect exists in the surrounding material.

As such, the present invention provides a bolt hole probe that is adjustable for use in bolt holes ranging in diameter from 0.200 inches to 0.600 inches, for example. The probe of the present invention can be used with existing eddy current testing equipment, and it is inexpensive to manufacture, easy to use, and reliable in use.

The present invention provides a sidewall deflection assembly that positively acts in both directions on the probe sidewalls to facilitate outward deflection and return thereof. In particular, the sidewall deflection assembly translates rotation of a knob or other operator into expansion or contraction of the effective diameter of the probe. Thus, the rotating mechanism on the existing eddy current testing equipment can be adapted to automatically adjust the effective diameter of the probe. Moreover, the central portion of each flexible sidewall moves along a line perpendicular to the axis of the bolt hole, so the eddy current coil mounted on this central portion remains in a fixed orientation relative to the bolt hole wall, regardless of the degree of deflection. These and other advantages of the present invention will become apparent to those skilled in the art upon a more detailed description of a preferred embodiment.

BRIEF DESCRIPTION OF THE DRAWING

In the Figures, wherein like numerals represent like parts and assemblies throughout the several views.

DETAILED DESCRIPTION OF A PREFERRED EMBODIMENT

Figure 1:
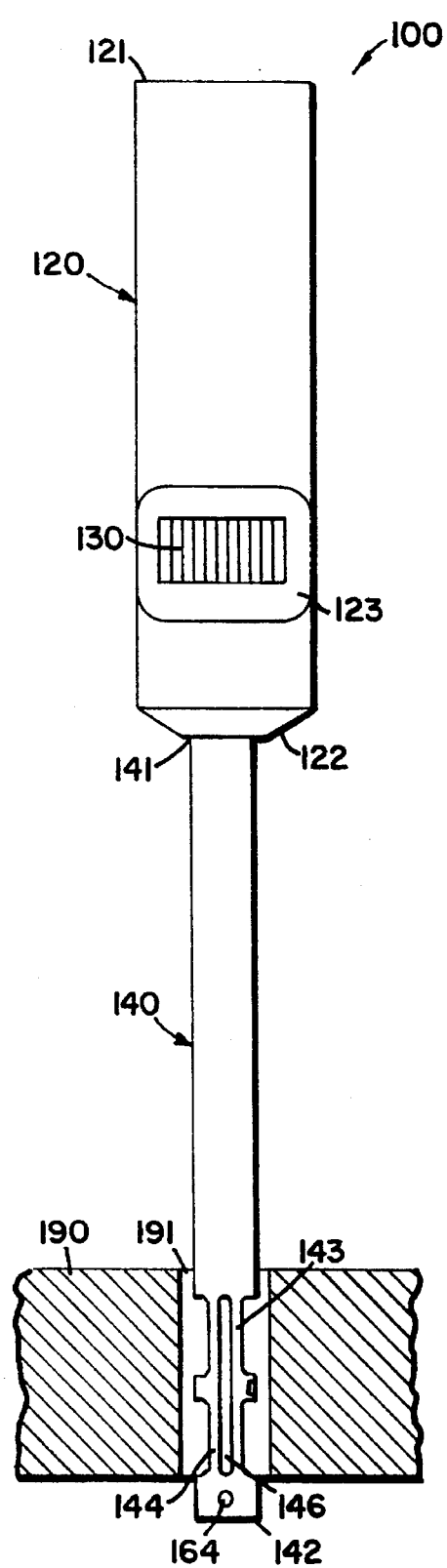
FIG. 1 is a front view of a preferred embodiment probe constructed according to the principles of the present invention and shown in relation to a bolt hole.
Figure 2:
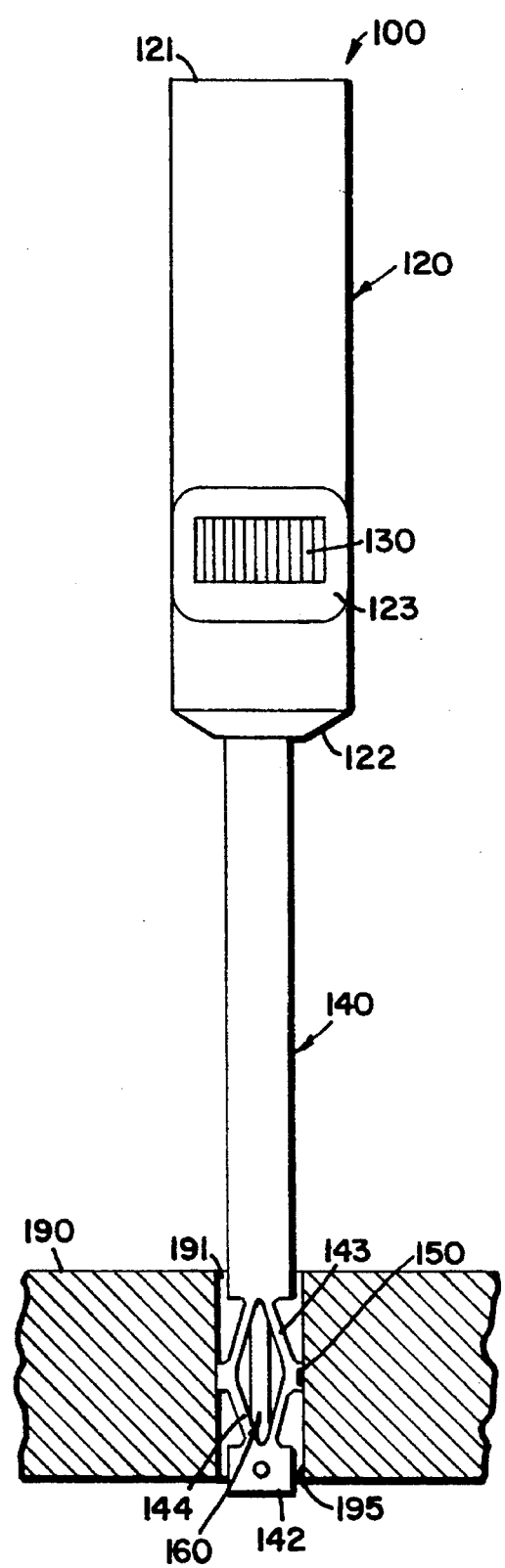
FIG. 2 is a front view of the probe and bolt hole shown in FIG. 1 with the sidewalls of the probe flexed radially outward to engage the wall of the bolt hole.

A preferred embodiment eddy current probe constructed according to the principles of the present invention is designated as 100 in FIGS. 1 and 2. The probe 100 is used to detect defects in material surrounding bolt holes and the like. For example, FIGS. 1 and 2 show the probe 100 in relation to a bolt hole 191 extending through an aircraft part 190.

The probe 100 generally includes a handle 120 having an upper end 121 and a lower end 122, a tube 140 having an upper end 141 and a lower end 142, and a shaft 160 having an upper end 161 and a lower end 162. The upper end 141 of the tube 140 is secured to the lower end 122 of the handle 120, and the lower end 142 of the tube 140 is secured to the lower end 162 of the shaft 160. Additionally, the upper end 161 of the shaft 160 is movably mounted relative to the handle 120, as well as the tube 140.

Figure 3:
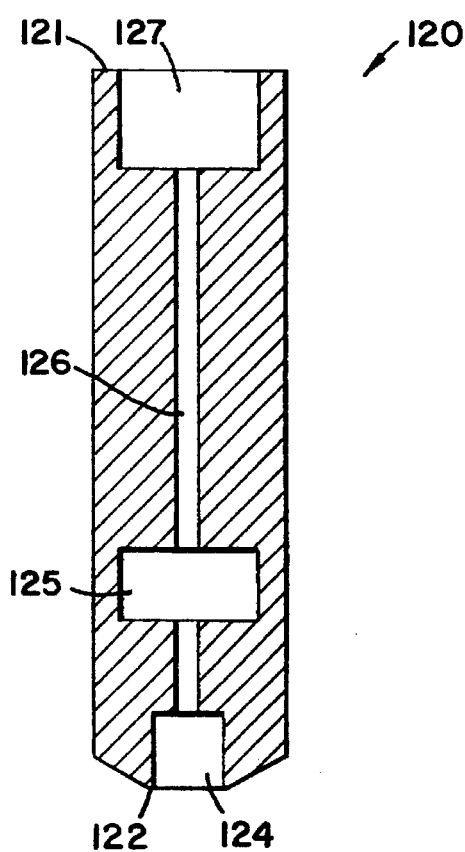
FIG. 3 is a front sectional view of the handle that is a part of the probe shown in FIG. 1.

In the preferred embodiment, the handle or first member 120 is an Aluminum rod that extends axially from the upper end 121 to the lower end 122. The external diameter of the handle 120 is substantially constant with the exception of a chamfer at the lower end 122 and a pair of diametrically opposed notches 123 formed in the sidewall proximate the lower end 122. As shown in FIG. 3, a lower bore 124 is formed in the lower end 122 of the handle 120 to receive the upper end 142 of the tube 140. The tube or second member 140 is made of polyurethane with wear additives. The tube 140 extends from the upper end 141 to the lower end 142 in axial alignment with the handle 120.

The tube 140 has a plurality of flexible sidewalls 143–145 disposed between the upper end 141 and the lower end 142, more proximate the latter. The external diameter of the tube 140 is substantially constant with the exception of the sidewalls 143–145, which are formed by grinding away outer portions of the tube material to create two smaller diameter sections having relatively thinner walls. The sidewalls 143–145 are then separated from one another by axially extending slits 146 that are spaced approximately 120 degrees apart to define three sidewalls of comparable size.

By definition, the tube 140 is hollow, and the shaft 160 is disposed within the interior of the tube 140. The shaft or third member 160 is a portion of a stainless steel hypodermic needle, and it extends from the upper end 161 to the lower end 162 in axial alignment with the handle 120 and the tube 140. The lower end 162 of the shaft 160 is secured to the lower end 142 of the tube 140 by means of a pin 164 that passes through corresponding holes formed in the tube lower end 142 and the shaft lower end 162. The pin hole in the shaft 160 is designated as 166 in FIG. 4.

Figure 4:
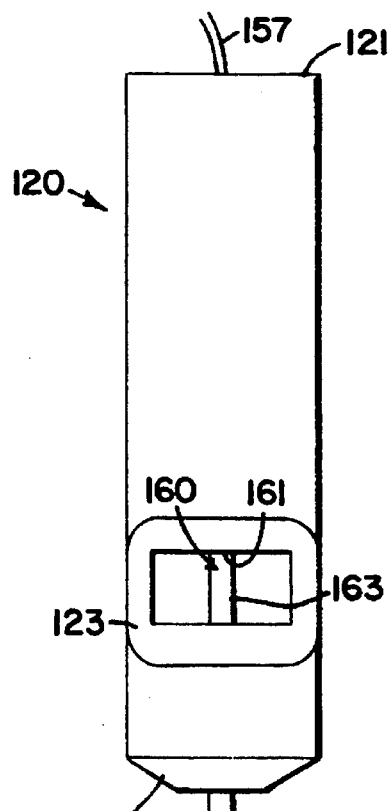
FIG. 4 is a front view of the handle and the shaft that are parts of the probe shown in FIG. 1.
Figure 5:
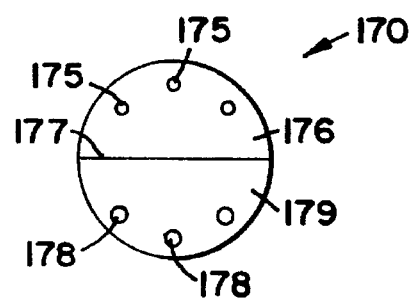
FIG. 5 is a top view of the connector that is a part of the probe shown in FIG. 1.
Figure 5:
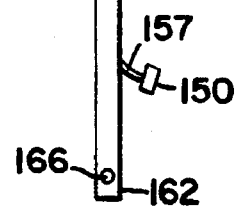

As shown in FIG. 3, an intermediate bore 126 is formed in the handle 120 between the lower bore 124 and an upper bore 127. The intermediate bore 126 receives the upper end 162 of the shaft 160, which extends upward beyond the upper end 141 of the tube 140. As shown in FIG. 4, threads are disposed on a portion of the shaft upper end 161. An opening 125 is formed through an intermediate portion of the handle 120 to accommodate a knob 130, which has internal threads that are sized and configured to mate with the external threads on the shaft upper end 161. The shaft upper end 161 is threaded through the knob 130 and maintains the knob 130 in axial alignment with the handle 120 and the tube 140, as well as the shaft 160. The confines of the opening 125 prevent axial travel of the knob 130 relative to the handle 120. The diametrically opposed notches 123 are formed in the sidewall of the cylinder to provide access to the knob 130.

Rotation of the knob 130 is linked to axial movement of the shaft 160 relative to the handle 120 and all but the lower end 142 of the tube 140. Rotation of the knob 130 in a first direction causes the shaft 160 to travel upward toward the handle 120, but only to the extent that the flexible sidewalls 143–145 are capable of flexing radially outward from the shaft 160 to accommodate "shortening" of the tube 140. In this compressed stage, shown in FIG. 2, rotation of the knob 130 in a second, opposite direction causes the shaft 160 to travel downward away from the handle 120 and the sidewalls 143–145 to straighten back radially inward toward shaft 160. The travel of the shaft 160 relative to the knob 130 is limited by the length of the threads on the shaft upper end 161.

Figure 6:
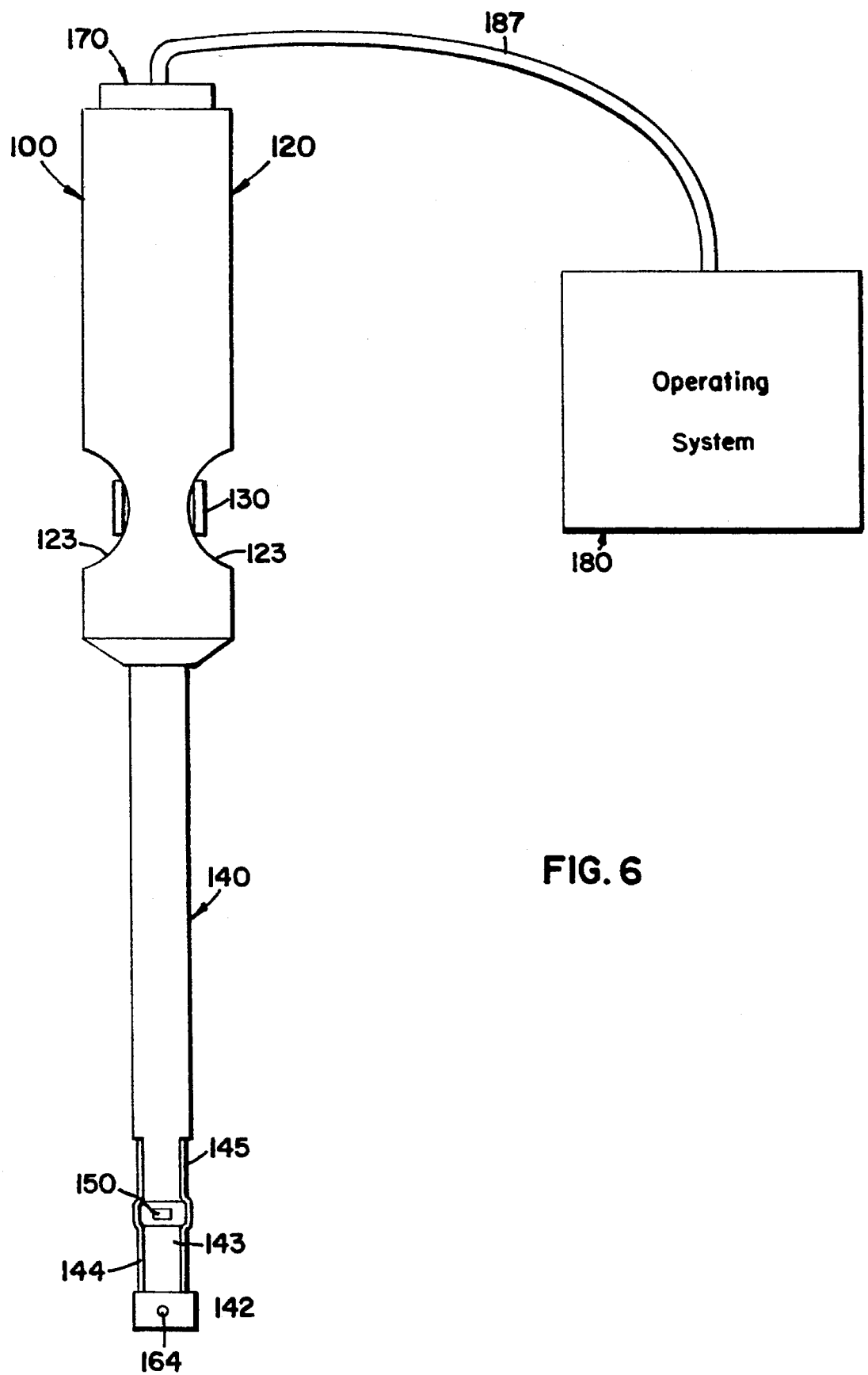
FIG. 6 is a side view of the probe shown in FIG. 1 with the probe connected to an operating system.

Each of the flexible sidewalls 143–145 has a central portion that is not subjected to the grinding process and thus, retains the same curvature and wall thickness as the bulk of the tube 140. As shown in FIG. 2, these protuberances engage the internal wall of the bolt hole 191 as the flexible sidewalls 143–145 deflect radially outward. As shown in FIGS. 2 and 6, an eddy current coil 150 is mounted on the protuberance of the flexible sidewall 143, and the coil 150 travels perpendicularly away from the axis of the bolt hole 191 as the flexible sidewalls 143–145 deflect radially outward. Thus, the coil 150 remains in a fixed orientation relative to the bolt hole wall 195, even at maximum deflection of the sidewalls 143–145.

The coil 150 is connected to a plug or connector 170 by means of a wire (designated as 157 in FIG. 4), which extends through the bore in the shaft 160. The plug 170 fits in the upper bore 127 formed in the upper end 121 of the handle 120. The plug 170 has a lower surface 176 and an upper surface 179 with a perpendicular edge 177 disposed therebetween. Pins 175 extend upward from the lower surface 176, and pin receptacles 178 extend downward through the upper surface 179 for purposes of connecting the probe 100 to a conventional operating system 180 (shown in FIG. 6) via a cable 187. The upper end 121 of the handle 120 is secured to the operating system 180 by means of a chuck assembly that selectively clamps and maneuvers the probe 100. The operating system 180 also includes means for energizing the eddy current coil 150 within a bolt hole and for analyzing whether a defect exists in the material surrounding the bolt hole.

The present invention is described with reference to a preferred embodiment, but additional embodiments and applications fall within the scope of the present invention. For example, although the preferred embodiment is described with reference to a handle and the diameter of the probe is adjusted by hand, this manual mode of operation is not a limiting feature. By substituting a counterweight for the knob 13D, one can take advantage of the rotation mechanism of the operating system to self-adjust the probe to any diameter within the available range of diameters. Accordingly, the present invention is limited only by the following claims.

I claim:

1. An eddy current probe, comprising:

a tube having a longitudinal axis and having flexible sidewalls extending substantially parallel to said longitudinal axis;

an eddy current coil mounted on at least one of said flexible sidewalls; and a shaft connected to and movably mounted within said tube, wherein axial movement of said shaft relative to said flexible sidewalls causes radial deflection of said flexible sidewalls relative to said longitudinal axis.

2. An eddy current probe according to claim 1, wherein said tube extends axially from a first tube end to a second tube end, and said flexible sidewalls are intermediate said first tube end and said second tube end.

3. An eddy current probe according to claim 2, wherein said shaft has a longitudinal axis and extends axially from a first shaft end to a second shaft end, and said second shaft end is secured to said second tube end so that said second tube end moves together with said second shaft end, and said flexible sidewalls deflect away from said longitudinal axis in response to movement of said second tube end toward said first tube end.

4. An eddy current probe according to claim 3, further comprising a knob that is free to rotate about said longitudinal axis of said tube but barred against movement along said longitudinal axis of said tube, wherein said knob has internal threads that mate with external threads on said first shaft end, and rotation of said knob about said longitudinal axis of said tube causes linear movement of said shaft along said longitudinal axis of said tube.

5. An eddy current probe according to claim 2, wherein said tube has a plurality of flexible sidewalls, and each of said plurality of flexible sidewalls is an elongate strip with an intermediate section that protrudes radially outward.

6. An eddy current probe according to claim 1, wherein said tube has three flexible sidewalls spaced approximately 120 degrees apart and separated from one another by axially extending slits in said tube.

7. An eddy current probe according to claim 1, further comprising a connecting means for connecting the probe to an operating system, wherein at least a portion of said shaft is hollow, and said connecting means includes a wire disposed within said shaft and connected to said coil.

8. An eddy current probe according to claim 1, further comprising moving means connected to said shaft for moving said shaft relative to said tube.

9. An eddy current probe according to claim 8, wherein said moving means is free to rotate about said longitudinal axis of said tube but barred against movement along said longitudinal axis of said tube, and rotation of said moving means about said longitudinal axis causes linear movement of said shaft along said longitudinal axis.

10. An eddy current probe according to claim 9, wherein said moving means includes a knob having internal threads that mate with external threads on said shaft.

11. An eddy current probe, comprising:

a first member;

a second member extending between a first end that is secured to said first member, and a second, opposite end;

flexible sidewalls disposed between said first end and said second, opposite end of said second member, wherein said flexible sidewalls deflect in response to relative movement of said first end and said second end of said second member;

a third member having a first end movably secured relative to said first member, and a second, opposite end secured to said second, opposite end of said second member;

a moving means connected to said third member, for moving said third member relative to said first member, wherein movement of said third member relative to said first member causes relative movement of said first end and said second end of said second member, thereby causing deflection of said flexible sidewalls; and an eddy current sensing means on at least one of said flexible sidewalls.

12. An eddy current probe according to claim 11, wherein said first member, said second member, and said third member are substantially cylindrical and share a common longitudinal axis, and said third member extends through central bores formed in said first member and said second member.

13. An eddy current probe according to claim 12, further comprising a connecting means for connecting the probe to an operating system, wherein said connecting means includes a wire connected to said eddy current sensing means, and said wire extends through a bore formed in said third member.

14. An eddy current probe according to claim 11, wherein said moving means includes a fourth member having internal threads that mate with external threads on said first end of said third member, wherein said fourth member is connected to said first member and said third member in such a manner that said fourth member is rotatable about an axis of rotation but barred against movement along said axis of rotation, whereby rotation of said fourth member causes movement of said third member along said axis of rotation.

15. An eddy current probe according to claim 14, wherein said fourth member occupies an opening formed in an intermediate portion of said first member.

16. An eddy current probe according to claim 11, wherein said second member has a fixed diameter, and said flexible sidewalls have protuberances that cooperate to define an effective diameter that is selectively variable through a range of diameters from said fixed diameter to a maximum diameter greater than said fixed diameter.

17. An eddy current probe according to claim 11, wherein said flexible sidewalls are integral portions of said second member.

18. An eddy current testing system of a type used to detect defects in material surrounding a bolt hole, comprising:

a probe having flexible sidewalls that are movable from first positions defining a first, relatively smaller effective diameter to second positions defining a second, relatively larger effective diameter;

a moving means connected to said probe for moving said flexible sidewalls between said first positions and said second positions, wherein said moving means includes a knob that rotates relative to said probe, and rotation of said knob in one direction moves said flexible sidewalls toward said second, relatively larger effective diameter, and rotation of said knob in an opposite direction moves said flexible sidewalls toward said first, relatively smaller effective diameter;

an eddy current coil secured to at least one of said flexible sidewalls; and an operating means connected to said probe for energizing said eddy current coil within a bolt hole and analyzing whether a defect exists in the material surrounding the bolt hole.

19. An eddy current testing system according to claim 18, wherein said probe includes a tube extending axially from a first tube end to a second tube end, and said flexible sidewalls are an integral portion of said tube, separated from one another by axially extending slits in said tube.

20. An eddy current testing system according to claim 19, wherein said moving means includes a connector extending from said second tube end to said knob, wherein rotation of said knob in said one direction causes said connector to pull said second tube end toward said first tube end, thereby causing said flexible sidewalls to flex outward toward said second positions.

* * * * *